US011266776B2

(12) United States Patent
Wen

(10) Patent No.: US 11,266,776 B2
(45) Date of Patent: Mar. 8, 2022

(54) METHOD AND APPARATUS FOR IRRIGATION

(71) Applicant: Medtronic Xomed, Inc., Jacksonville, FL (US)

(72) Inventor: Jie Wen, St. Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 14/928,066

(22) Filed: Oct. 30, 2015

(65) Prior Publication Data

US 2017/0119952 A1 May 4, 2017

(51) Int. Cl.
*A61M 3/02* (2006.01)
*A61M 11/00* (2006.01)
*A61M 39/22* (2006.01)
*A61M 39/24* (2006.01)
*A61M 5/31* (2006.01)

(52) U.S. Cl.
CPC ........ *A61M 3/0262* (2013.01); *A61M 3/0279* (2013.01); *A61M 5/3137* (2013.01); *A61M 11/007* (2014.02); *A61M 39/223* (2013.01); *A61M 39/24* (2013.01); *A61M 2005/3139* (2013.01); *A61M 2210/0681* (2013.01)

(58) Field of Classification Search
CPC ............. A61M 3/0262; A61M 11/007; A61M 3/0279; A61M 5/3137; A61M 39/223; A61M 39/24; A61M 2005/3139; A61M 2210/0681; A61M 3/0254; A61M 2205/32; A61M 2205/60; A61M 2205/58; A61M 2205/583; A61M 19/00; A61M 2025/0007; A61M 2025/0008; A61M 5/204; A61B 1/233
See application file for complete search history.

(56) References Cited

U.S. PATENT DOCUMENTS

| | | | |
|---|---|---|---|
| 1,496,126 A * | 6/1924 | Livingstone | A61M 1/0035 604/183 |
| 1,644,225 A | 10/1927 | Barth | |
| 3,214,775 A | 11/1965 | Murov et al. | |
| 3,452,745 A | 7/1969 | Hutchinson et al. | |
| 4,990,140 A * | 2/1991 | Black | A61M 3/0279 604/192 |

(Continued)

FOREIGN PATENT DOCUMENTS

| | | |
|---|---|---|
| AU | 2015200049 A1 | 2/2015 |
| JP | H0646666 A | 2/1994 |

(Continued)

OTHER PUBLICATIONS

International Search Report and Written Opinion dated Mar. 21, 2017 for PCT/US2016/058871 claiming benefit of U.S. Appl. No. 15/332,693, filed Oct. 24, 2016 and U.S. Appl. No. 15/332,693, filed Oct. 24, 2016.

(Continued)

*Primary Examiner* — Brandy S Lee
*Assistant Examiner* — Hong-Van N Trinh
(74) *Attorney, Agent, or Firm* — Harness, Dickey & Pierce, P.L.C.

(57) ABSTRACT

Disclosed is an irrigation system. The irrigation system includes a manual pump and refill. The manual pump can provide pressurized liquid through a tube at an outlet.

18 Claims, 2 Drawing Sheets

(56) References Cited

U.S. PATENT DOCUMENTS

Figure 1:
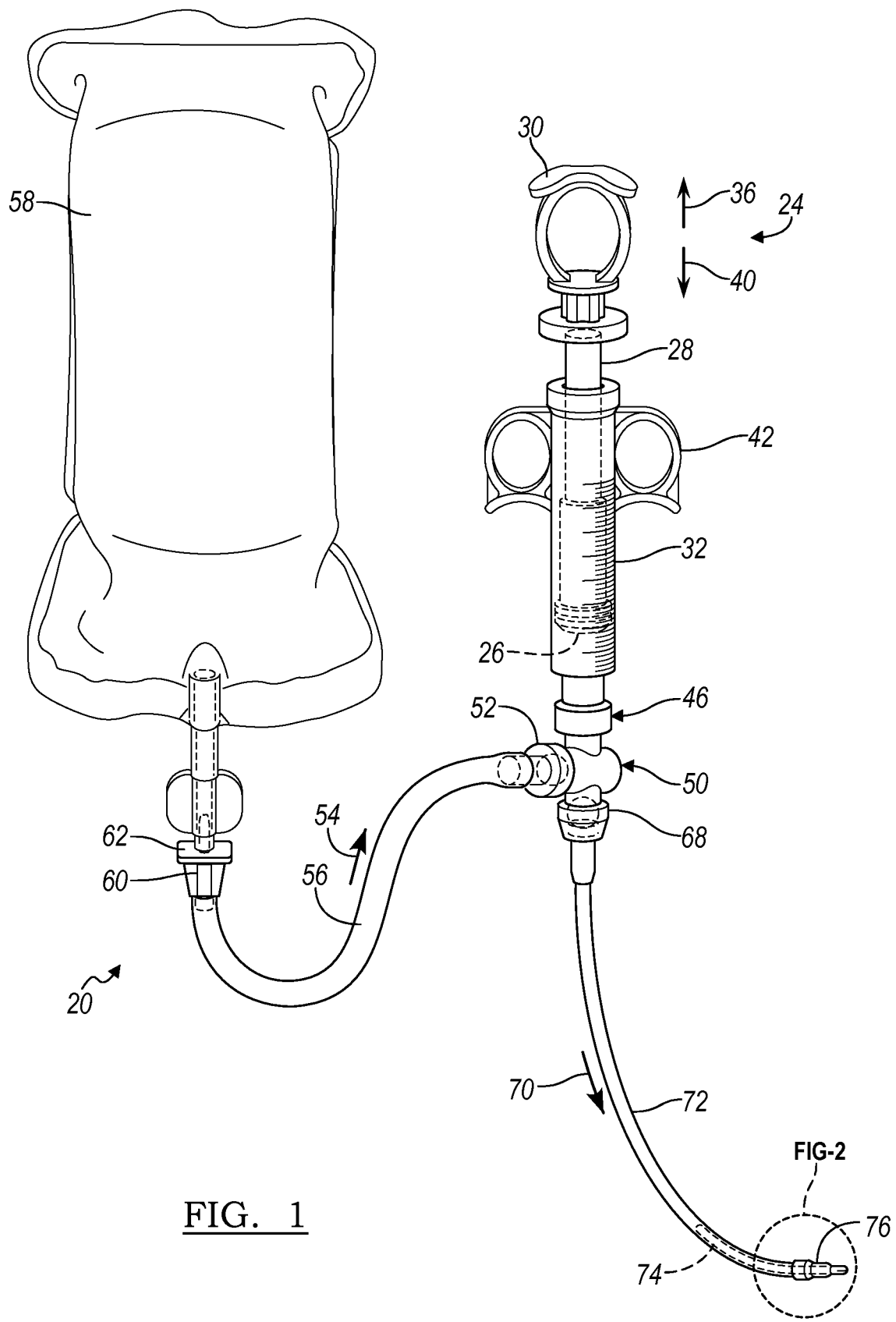

| | | | |
|---|---|---|---|
| 5,024,228 A | 6/1991 | Goldstone et al. | |
| 5,254,086 A | 10/1993 | Palmer et al. | |
| 5,264,260 A | 11/1993 | Saab | |
| 5,336,170 A * | 8/1994 | Salerno | A61M 3/0279 15/322 |
| 5,358,473 A | 10/1994 | Mitchell | |
| 5,591,135 A | 1/1997 | Sullivan | |
| 5,599,576 A | 2/1997 | Opolski | |
| 5,720,719 A * | 2/1998 | Edwards | A61B 10/0233 604/22 |
| 5,749,357 A * | 5/1998 | Linder | A61M 16/0429 128/200.26 |
| 5,766,158 A | 6/1998 | Opolski | |
| 5,807,340 A | 9/1998 | Pokras | |
| 5,968,017 A | 10/1999 | Lampropoulos et al. | |
| 6,200,292 B1 | 3/2001 | French et al. | |
| 6,543,452 B1 | 4/2003 | Lavigne | |
| 6,843,432 B1 * | 1/2005 | Philpott | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 8,206,349 B2 | 6/2012 | Slenker et al. | |
| 8,277,503 B2 | 10/2012 | Lavigne | |
| 8,594,805 B2 | 11/2013 | Hincapie Ordonez et al. | |
| 8,790,301 B2 | 7/2014 | Slenker et al. | |
| 9,037,226 B2 | 5/2015 | Hacker et al. | |
| 9,351,750 B2 | 5/2016 | Muni et al. | |
| 9,408,756 B2 | 8/2016 | Jenkins et al. | |
| 9,408,955 B2 | 8/2016 | Jenkins et al. | |
| 9,827,367 B2 | 11/2017 | Perry et al. | |
| 2004/0176738 A1 | 9/2004 | Paul et al. | |
| 2004/0254522 A1 * | 12/2004 | Kraus | A61M 27/006 604/9 |
| 2006/0095066 A1 * | 5/2006 | Chang | A61B 17/1688 606/199 |
| 2008/0183128 A1 | 7/2008 | Morriss et al. | |
| 2008/0289635 A1 * | 11/2008 | Hull | A61M 3/0279 128/845 |
| 2009/0270796 A1 * | 10/2009 | Perry | A61M 3/0216 604/35 |
| 2010/0114016 A1 * | 5/2010 | Gallo | A61H 35/04 604/73 |
| 2011/0009699 A1 | 1/2011 | Slenker et al. | |
| 2011/0112512 A1 | 5/2011 | Muni et al. | |
| 2013/0053926 A1 | 2/2013 | Hincapie Ordonez et al. | |
| 2013/0072958 A1 * | 3/2013 | Ressemann | |
| 2013/0184574 A1 * | 7/2013 | Newhauser, Jr | A61M 3/0279 600/431 |
| 2013/0274600 A1 * | 10/2013 | Jenkins | A61B 1/07 600/431 |
| 2014/0014869 A1 | 1/2014 | Fink et al. | |
| 2014/0180138 A1 | 6/2014 | Freeman et al. | |
| 2014/0276625 A1 | 9/2014 | Jenkins et al. | |
| 2014/0276654 A1 | 9/2014 | Jenkins | |
| 2014/0363801 A1 | 12/2014 | Samosky et al. | |
| 2015/0088029 A1 | 3/2015 | Wybo | |
| 2016/0038072 A1 | 2/2016 | Brown et al. | |
| 2016/0038073 A1 | 2/2016 | Brown et al. | |
| 2017/0119953 A1 | 5/2017 | Wen | |
| 2018/0042524 A1 | 2/2018 | Inman et al. | |

FOREIGN PATENT DOCUMENTS

| | | | |
|---|---|---|---|
| JP | H08509636 A | | 10/1996 |
| JP | 2000511804 A | | 9/2000 |
| JP | 2001519212 A | | 10/2001 |
| JP | 2006-528906 A | | 12/2006 |
| JP | 2011518643 A | | 6/2011 |
| JP | 2011-520563 A | | 7/2011 |
| WO | 9424969 A1 | | 11/1994 |
| WO | 9746161 A1 | | 12/1997 |
| WO | 9919008 A1 | | 4/1999 |
| WO | WO-2007134101 A2 | | 11/2007 |
| WO | 2009134577 A1 | | 11/2009 |
| WO | 2016064870 A1 | | 4/2016 |

OTHER PUBLICATIONS

Invitation to Pay Additional Fees dated Jan. 25, 2017 for PCT/US2016/058871 claiming benefit of U.S. Appl. No. 15/332,693, filed Oct. 24, 2016 and U.S. Appl. No. 15/332,693, filed Oct. 24, 2016.

Medtronic "Hydrodebrider Endoscopic Sinus Irrigation System" date accessed: Oct. 22, 2015 at website: http://www.medtronic.com//for-healthcare-professionals/products-therapies/ear-nose-throat/powered-ent-instruments/hydrodebrider-endoscopic-sinus-irrigation-system/.

Qosina 80187 "Dual Check Valve" 2 pages; date acesed: Oct. 30, 2015 at website: http://www.qosina.com/dual-check-valve-male-luer-lock-outlet-port-female-luer-slip-inlet-port-and-female-luer-lock-control-port-80187.

BD Cornwall—305224 "Fluid Dispensing Syringe" 2 pages; date accesssed: Aug. 30, 2016 at website: http://catalog.bd.com/nexus-ecat/getProductDetail?productId-305224.

International Preliminary Report on Patentability dated May 11, 2018 in corresponding International Application No. PCT/US2016/058871.

International Search Report and Written Opinion dated Nov. 14, 2017 in corresponding International Application No. PCT/US2017/046312.

Schneider et al. "Continuous intraoperative vagus nerve stimulation for identification of imminent recurrent laryngeal nerve injury: Continuous IONM for Thyroid Surgery", Head and Neck, vol. 35, No. 11, Nov. 1, 2013, pp. 1591-1598, XP055421596, US ISSN: 1043-3074, DOI 10.1002/hed.23187.

MEMS Enable Medical Innovation by Mouser Electronics, Inc. May 4, 2015.

International Preliminary Report on Patentability dated Feb. 21, 2019 in corresponding International Application No. PCT/US2017/046312.

Office Action dated May 28, 2020 in corresponding/related Chinese Application No. 201680073548.6.

Examination Report dated Jul. 9, 2020 in corresponding/related Australian Application No. 2016346327.

Office Action dated May 25, 2020 in corresponding/related European Application No. 16790856.5.

Office Action dated Nov. 9, 2020 in corresponding/related Japanese Application No. 2018-522030.

Office Action regarding Japanese Patent Application No. 2018-522030 (with English Translation), dated Apr. 30, 2021.

Second Office Action regarding corresponding Chinese Application No. 201680073548.6, dated Apr. 6, 2021.

Office Action dated Nov. 16, 2021, in corresponding Chinese Application No. 201680073548.6.

* cited by examiner

METHOD AND APPARATUS FOR IRRIGATION

FIELD

The subject disclosure relates to an irrigation system, and particularly relates to a manually powered irrigation system having a nozzle.

BACKGROUND

This section provides background information related to the present disclosure which is not necessarily prior art.

During selected procedures, it may be selected to provide a liquid to a specific location. Generally, fluid may be delivered through a tube that may be powered by a pump. Further, the tube may include suction portions to withdraw/remove material and/or irrigation liquid from a site. Selected systems include a Hydrodebrider® pressurized sinus irrigation system sold by Medtronic, Inc. and systems such as those disclosed in U.S. Patent Application Publication Nos. 2009/0270796 and 2011/0009699 and U.S. Pat. Nos. 8,790,301 and 8,206,349. Such systems are disclosed to include a vacuum source and a control to control a vacuum and irrigation.

SUMMARY

This section provides a general summary of the disclosure, and is not a comprehensive disclosure of its full scope or all of its features.

According to various embodiments, a manual pump may be fitted with a valve system. The manual pump may include a syringe or other hand-held and/or operated pump mechanism. The valve system may allow for unidirectional or one-directional delivery of a fluid.

The valve system may include two one-way valves to allow for filling of a syringe barrel during a first movement of a syringe piston and delivery of a liquid from the filled barrel during a second motion of the piston. The valve system, therefore, allows for generally continuous delivery of a fluid from a source to a selected area while connected to a source.

Delivery of the fluid may be through a nozzle to provide a selected pressure of fluid to an irrigation site. Irrigation sites may include both living and non-living sites. For example, body surfaces, such as nasal and sinus cavities, or work surfaces, such as degreasing. During irrigation, the pressure may assist in loosening or removing a selected material from a selected surface or breaking up large agglomerations of material into smaller portions for removal.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
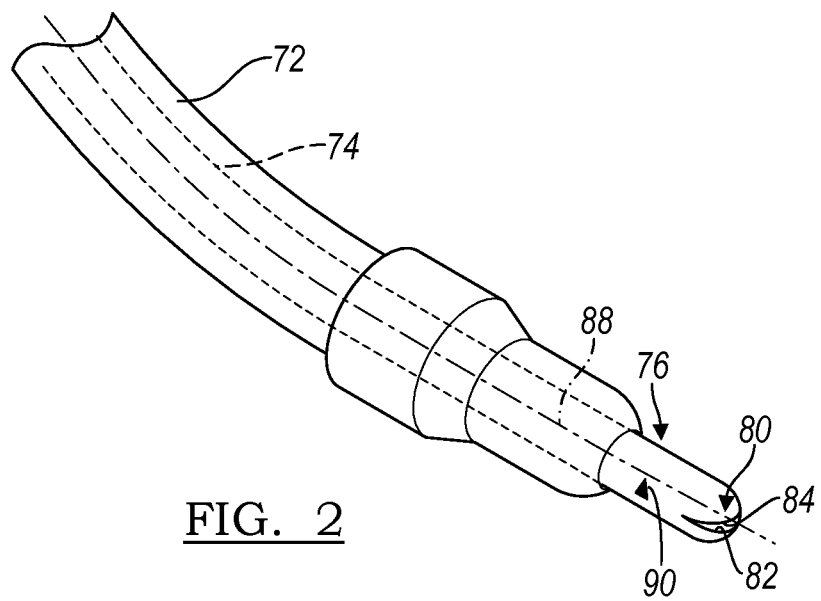
Figure 3:
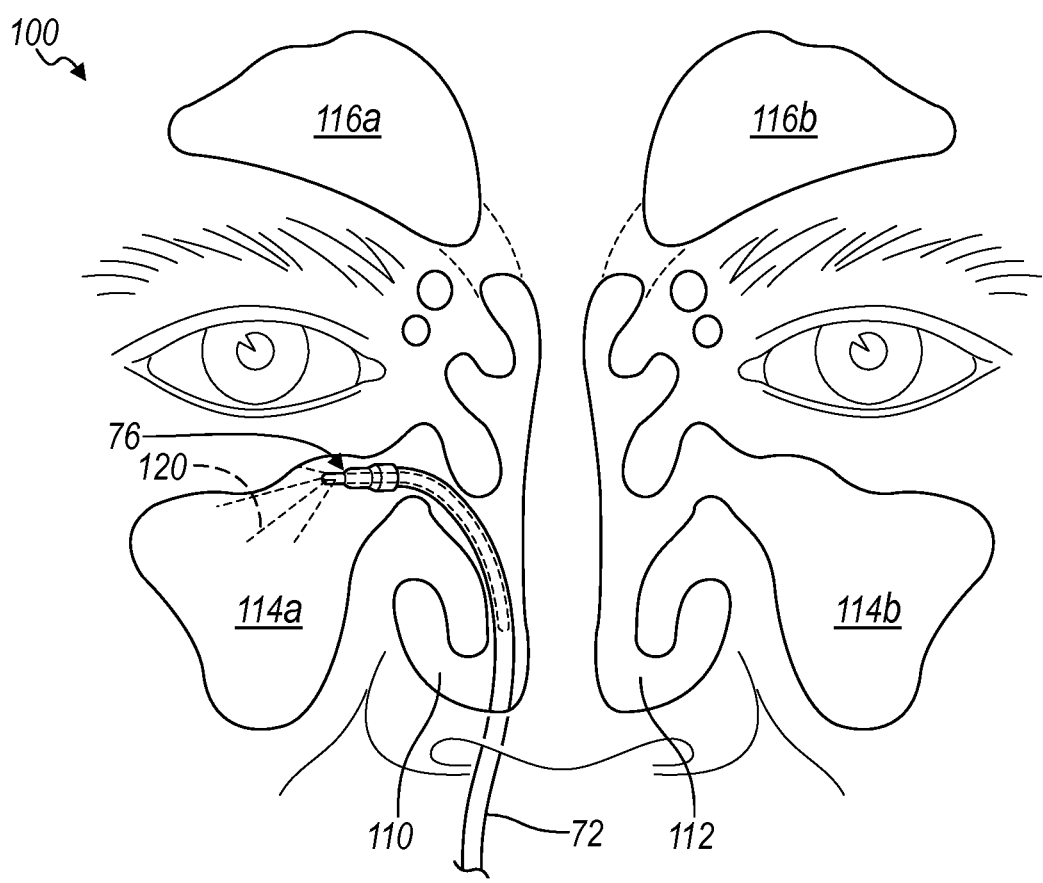

FIG. 1 is a plan view of an irrigation assembly;
FIG. 2 is a detailed end view of an irrigation nozzle; and
FIG. 3 is a schematic environmental view of an irrigation site.

Corresponding reference numerals indicate corresponding parts throughout the several views of the drawings.

DETAILED DESCRIPTION

Example embodiments will now be described more fully with reference to the accompanying drawings.

With initial reference to FIG. 1, an irrigation system 20 is illustrated. The irrigation system 20 is generally a manual irrigation system powered by a user that holds a manual pump system or syringe assembly 24 in one or more hands to operate the syringe assembly 24. The syringe assembly 24 may include a piston head 26 interconnected with a piston rod 28. The piston rod 28 may include various features such as a thumb hole or loop 30 to assist in operation of the syringe assembly 24 with one hand of a human user.

The syringe assembly 24 may include various features such as further including finger or digit rings 42 to assist in manipulating the syringe assembly 24, in addition to the thumb ring 30, again with one hand of a human user. Further, a connection portion 46 may include connection mechanisms such as a Luer-Lok® syringe connection, twist lock, press fit, or the like. Therefore, a mechanism may be interconnected with the syringe assembly 24 for use of the irrigation assembly 20.

As is generally understood by one skilled in the art, the syringe assembly 24 may be operated to fill a pump volume or syringe barrel 32 by moving the piston head 26 with the piston rod 28 generally in the direction of arrow 36 and may be emptied by moving the piston head 26 with the piston rod 28 generally in the direction of arrow 40. It is understood, however, that the syringe assembly 24 may also have a self-return or self-priming system. Self-return systems may include a spring (not illustrated) to bias the piston head 26 away from the connection 46 generally in the direction of arrow 36. The user, to express the material from the syringe, would overcome the biasing force of the spring to express the material and the biasing force would assist in moving or move the piston head away from the connection 46 to refill the syringe barrel.

Connected with the syringe assembly 24 at the connection region 46 may be a valve assembly 50. The valve assembly 50 may include the dual check valve 80187 sold by Qosina, having a place of business at Ronkonkoma, N.Y. The valve assembly 50 may include various valve portions, including two one-way valves. The two one-way valves may include a first one-way valve assembly 52 that opens when negative pressure is formed within the valve assembly 50. Negative pressure may be produced when the piston head 26 moves generally in the direction of allow 36 to allow a flow of material through the one-way valve assembly 52 generally in the direction of arrow 54. The material may flow generally in the direction of arrow 54 through a tubing 56. The tubing 56 may be a flexible tubing to connect with a source container 58 holding or containing a volume or liquid, such as an irrigant liquid.

The source container 58 may be a container, such as an IV bag or other appropriate volume of an irrigation fluid. The irrigation fluid may be a selected material such as saline. The irrigation fluid may further include various therapeutic reagents such as antibacterial, antimicrobial, anti-inflammatory, and wound healing components.

The tubing 56 may be connected with a connector 60 to a connection receptacle 62 of the irrigant volume container. The connector 60 and the connection 62 can be any appropriate connection members, as is generally understood in the art. The connection of the connector 60 with the connector 62 may generally be an open connection such that fluid will generally flow from the source container 58 through the tubing 56 once the connector 60 is connected with a connection 62. The one-way valve assembly 52, however, may control flow of the fluid from the source container 58 to the syringe assembly 24, including within the barrel 32.

Accordingly, as noted above, when the piston head 26 generally moves in the direction of arrow 36, the irrigant is drawn from the source container 58 through the connection 62 and the connector 60 through the tubing 56 and generally in the direction of arrow 54. The movement of the piston head 26 in the direction of arrow 36 may cause a negative pressure through the connector 46 to the valve assembly 50 to open the one-way valve 52. Therefore, the syringe barrel 32 fills with the irrigant fluid.

Once a selected volume of the irrigant is positioned within the barrel 32, however, movement of the syringe piston head 26 in the direction of arrow 36 may be ceased. The piston head 26 may then be moved in the direction of arrow 40 to move the piston head 26 generally towards the connector 46 to assist in removing or evacuating the irrigant material from the barrel 32.

When the piston head 26 is moved generally in the direction of arrow 40, the pressure at the valve assembly 50 may be increased. The increased pressure in the valve assembly 50 can close the one-way valve 52 and open a one-way valve assembly 68. The increased pressure at the one-way valve assembly 68 may cause the one-way valve 68 to open to allow the irrigant to flow from the barrel 32 through the valve assembly 50 and generally in the direction of arrow 70 through an evacuation or irrigant tubing 72. The irrigation tubing 72 may extend along a selected length and may bend according to a selected configuration.

The tubing 72 may be formed of a material that may be rigid or bendable. In various embodiments, the tubing 72 may be bent for use and may maintain the selected bent configuration. Alternatively, or in addition thereto, the tubing 72 may only be flexible and a bendable support structure 74 may be positioned at at least a region of the tubing 72 to assist in supporting and holding the tubing 72 in a selected shape. According to various embodiments, the structure 74 may be a malleable tube, such as an aluminum tube, fixed within the tubing 72. Various embodiments, may also include malleable wires embedded in a wall of the tubing 72. Further, multiple tubes may be concentrically placed to support a bend. In still further various embodiments, a distal tube may be formed of a second material different from a proximal portion of the tubing 72 that may be malleable.

The tubing 72 may be bent at a selected radius, such as near a tip 76 to assist in positioning the tip 76 at a selected location. For example, the tip 76 may be selected to be positioned in a sinus cavity, as discussed further herein, and forming a radius or angle near the tip 76 may assist in positioning the tip 76 within the selected sinus. The radius may be supported by the structure 74 that may be different than the material of the tubing 72.

With continued reference to FIG. 1 and additional reference to FIG. 2, the tip 76 may be formed to cause a selected shape of a spray that exits the tube 72 and the tip 76. As illustrated in FIG. 2, a detailed view generally along or at the distal tip 76 of the irrigation tube 72 is illustrated. The tip 76 may include a selectively shaped opening 80. The opening 80 may include a slit that has a first surface 82 and a second surface 84. The first and second surfaces 82, may be angled relative to one another and may include an elongated configuration such that a fan-shaped spray emanates from the tip 76. The opening 80 may also include sidewalls adjacent to the surfaces 82, 84 to further direct the spray.

At the tip 76, the first surface 82 may be angled relative to the second surface 84 to form a selected configuration of the spray, as noted above, which may be a fan shape. Further, due to the angle of the surface 84, the spray may be directional, such as spraying generally at the angle of the surface 84 and away from an axis 88 through the tip 76. This can allow the tip 76 to be rotated around the axis 88, such as by rotating the syringe assembly 24, to select a direction of the spray through the opening 80.

Visualization of the direction of the spray may be made by direct endoscopic or direct visual inspection of the spray. Further, a directional marker, such as a radiopaque indicator 90 may be included to indicate a direction of the spray from the opening 80. For example, as illustrated in FIG. 2, a triangle or arrowhead may be the indicator 90 that points towards the direction of the spray. Therefore, a fluoroscopic view may be made to determine the direction of the spray from the opening 80.

Further, a cross-sectional area or volume of the opening 80 relative to a cross-sectional area of an opening or lumen through the tubing 72 may be selected at an appropriate ratio of about 1:1 to about 1:10,000, including about 1:2 to about 1:100, including about 1:6. Further, more than one of the tips 76 may be provided on the tubing 72. Multiple tips or multiple openings on one tip may provide for a spray being directed in a plurality of directions at once. Further, the tips 76 may be selectable or changeable during use. Different tips providing different ratios may be used to provide different spray patterns and/or pressures. Accordingly, a kit may be provided that includes the irrigation system 20 with one or more tips 76. The tips may be assembled during use. The kit may be provided in a container that allows sterilization of the kit prior to use. The ratio of the volume of the opening 80 relative to cross-sectional area of the lumen can allow for a selected pressure to be provided through the opening 80. Providing a selected pressure, such as a pressure of about 1 pounds per square inch (PSI) to about 100 PSI may be provided. The selected PSI may assist in a procedure, such as debridement of a region. For example, debridement may include removing a biofilm, breaking an agglomeration, or otherwise providing pressure to an area to assist in removing a selected material or clearing a selected area.

With continuing reference to FIGS. 1 and 2 and additional reference to FIG. 3, the irrigation assembly 20 may be used to debride or irrigate a selected nasal passage or sinus cavity. As is generally understood by one skilled in the art, a subject, such as a human subject 100 may include or have a first nasal passage 110 or a second nasal passage 112. Further, the subject 100 may include one or more sinus cavities including schematically illustrated sinus cavities, including maxillary sinuses 114a and 114b and frontal sinuses 116a and 116b.

During a procedure, the tip 76 may be introduced through the nasal passage 110 and moved into the maxillary sinus cavity 114a. The tip 76 may be carried on the tubing 72 and may be manipulated into position via holding and operating the syringe assembly 24. During use, the user may then move the syringe head 26 generally in the direction of arrow 36 to fill the barrel 32 and then generally in the direction of arrow 40 to express the irrigation material through the tubing 72 and out of the tip 76.

When expressing the irrigation material out of the tubing 72 and tip 76, a spray 120 may be formed as the irrigation fluid impinges upon an internal surface of the maxillary cavity 114a. It is understood that the tip 76 may be moved through either or both of the nasal passages 110, 112 into any of the selected sinus cavities, including either of the maxillary sinuses 114a or 114b, or frontal sinuses 116a or 116b or other sinuses such as the sphenoid or ethmoid sinuses. Nevertheless, the user may operate the syringe assembly 24 to irrigate the sinus cavities and/or nasal passages.

During operation, the user may continuously irrigate using a reciprocating action of the piston head 26. By first moving the piston head 26 generally in the direction of arrow 36, the barrel 32 may be filled and then expressing material by moving the piston head 26 generally in the direction of arrow 40. As noted herein, the repeated movement of the piston head 26 in the first direction arrow 36 then the second direction arrow 40 a continuous irrigation may be performed.

The reciprocating motion of the piston head 26 may be manually operated by the user and may not cause a continuously steady stream (e.g. the continuous flow may be pulsatile) during the emptying of the source container 58. However, due to the connection of the syringe assembly 24 to the irrigation volume 58 through the tubing 56 and the position of the valve assembly 50, the source container 58 may be emptied or continuously used until debridement or irrigation is complete or the source container 58 is empty. Therefore, the user need not remove the syringe assembly 24 from the irrigation site to refill the syringe assembly 24 during an irrigation procedure, but may maintain the tip 76 at a selected irrigation position during an entire irrigation procedure while manually operating the syringe assembly 24 during the irrigation procedure.

It is understood that the irrigation assembly, according to various embodiments, as discussed herein, may be used to irrigate selected surfaces or volumes. FIG. 3 is merely exemplary of irrigating a surface or cavity within a human subject. It is understood, however, that other cavity within a subject may be irrigated. Further, devices, such as implants or treatment devices, may have the irrigant applied to their surfaces before, during, or after positioning within a subject. For example, an implant may have its surface irrigated after implantation to assist in removing an infection, etc.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for irrigation of a selected location, comprising:
 a container configured to contain a selected volume of a liquid, the container having a connection receptacle;
 a manual pump system having a pump volume, wherein the manual pump system is configured to be powered and operated by a user to move the liquid from the container;
 a first one-way valve configured to control flow of the liquid from the container to the pump volume;
 a container tubing having a connector at a first end connected to the connection receptacle of the container and a second end connected to the first one-way valve;
 a plurality of selectable tips, each tip having an opening to deliver a selected pressure spray of the liquid to a surface;
 a tubing extending from a proximal end at the pump volume to a distal end configured to be selectively connected to each tip of the plurality of tips, the tubing being only flexible;
 a bendable support structure formed of a material different than the tubing, but fixed to and within the distal end of the tubing adjacent a one tip of the plurality of selectable tips connected to the tubing that is configured to be bent to support and hold the tubing in a selected shape, such as a radius or angle, at the one tip to assist in positioning the one tip at the selected location; and
 a second one-way valve configured to control flow of the liquid from the pump volume to the one tip;
 wherein the bendable support structure extends from the one tip to a position within the flexible tubing spaced apart from the proximal end of the flexible tubing;
 wherein the manual pump system is configured to be reciprocally operated by the user to irrigate the selected location with the liquid through the ones tip positioned at the selected location with the bendable support structure fixed to and within the distal end of the tubing.

2. The system of claim 1, wherein the manual pump system includes a syringe having:
 a piston head and a piston rod moveable within the pump volume with a thumb loop connected to the piston rod; and
 a syringe barrel having a pair of digit rings forming the pump volume;
 wherein the user moves the piston head with the piston rod using the thumb loop and pair of digit rings to power and operate the manual pump system with a single hand of the user.

3. The system of claim 2, further comprising:
 a valve assembly including the first one-way valve and the second one-way valve;
 wherein the valve assembly is coupled to the syringe barrel;
 wherein the first one-way valve opens when the piston head moves in a first direction and the second one-way valve opens when the piston head moves in a second direction.

4. The system of claim 2, further comprising:
 a valve assembly including the first one-way valve and the second one-way valve;
 wherein the valve assembly is coupled to the syringe barrel;
 wherein the first one-way valve opens when the piston head moves in a first direction to form a vacuum in the syringe barrel and the second one-way valve opens when the piston head moves in a second direction to increase pressure in the valve assembly.

5. The system of claim 2, wherein the first one-way valve and the second one-way valve are operably connected to the syringe barrel to allow continuous operation of the manual pump system with the piston head and the piston rod during irrigation of the selected location with the liquid from the container.

6. The system of claim 1, wherein each tip of the plurality of selectable tips is configured for irrigation of a sinus portion;
wherein the opening of one of the plurality of tips has a cross-sectional area ratio relative to a cross-sectional area of the tubing extending from the pump volume of about 1:1 to about 1:10,000.

7. The system of claim 1, further comprising:
a valve assembly including the first one-way valve and the second one-way valve;
wherein the valve assembly is coupled to the manual pump system.

8. The system of claim 1, wherein the bendable support structure is a malleable tube and the flexible tubing is positioned concentric with the malleable tube.

9. The system of claim 1, wherein the bendable support structure is malleable wires embedded in a wall of the tubing.

10. A system for irrigation of a selected location, comprising:
a container configured to contain a selected volume of a liquid, the container having a connection receptacle;
a manual syringe system having a piston head interconnected with a piston rod having a thumb loop, where the piston head and the piston rod are moveable within a syringe barrel having a pair of connected digit rings to form a pump volume, wherein the piston head and the piston rod are configured to be powered and operated by a single hand of a user with the thumb loop and the pair of digit rings wherein the syringe barrel includes a connector at an end;
a valve assembly configured to be connected to the connector, including:
a first one-way valve configured to control flow from the container to the pump volume, and
a second one-way valve configured to control flow from the pump volume;
a container tubing having a connector at a first end connected to the connection receptacle of the container and a second end connected to the first one-way valve;
a plurality of selectable tips, each tip configured to be fluidly connected to the second one-way valve and having an opening to deliver a selected pressure spray to the selected location;
a flexible tubing coupled at a proximal end to the valve assembly and extending from the syringe barrel configured to be bent to be placed in the selected location at a distal end, wherein the distal end is configured to be selectively connected to each tip of the plurality of selectable tips, wherein the flexible tubing is only flexible; and
a bendable support tube that is fixed to and within the distal end of the flexible tubing adjacent each tip of the plurality of tips to support and hold the flexible tubing in a selected shape at each tip to assist in positioning each tip at the selected location;
wherein the bendable support tube extends from each tip to a position within the flexible tubing spaced apart from the proximal end of the flexible tubing;
wherein the manual syringe system is configured to be reciprocally operated by the single hand of the user to continuously irrigate the selected location with the liquid through each tip positioned at the selected location with the bendable support tube fixed to and within the distal end of the tubing.

11. The system of claim 10, wherein the piston head and the piston rod are configured to be powered and operated by the single hand of the user by using the thumb loop and the pair of digit rings to move the piston head and piston rod in a first direction to drain fluid from the container to the pump volume and to move the piston hand and the piston rod in a second direction to flow fluid from the pump volume to each tip.

12. The system of claim 11, wherein the piston head is configured to be moved in the first direction within the syringe barrel to reduce a pressure in the syringe barrel and the valve assembly thereby closing the second one-way valve and opening the first one-way valve and draw the liquid from the container into the pump volume.

13. The system of claim 12, wherein the piston head is configured to be moved in the second direction within the syringe barrel to increase a pressure in the syringe barrel and the valve assembly thereby opening the second one-way valve and closing the first one-way valve and to express the liquid from the pump volume through each tip.

14. The system of claim 13, wherein the second direction is opposite the first direction within the syringe barrel.

15. The system of claim 10, wherein the opening in each one tip of the plurality of tips is a slit that has a first surface angled relative to a second surface configured to cause a fan-shaped spray of liquid and a directional flow spray at an angle from each tip that angles away from a longitudinal axis through each tip, such that rotation of each tip selects a direction of the spray from each tip.

16. The system of claim 15, wherein each tip further includes a directional marker that points toward a direction of spray from the tip.

17. The system of claim 10, wherein the flexible tubing is formed of a first material and the bendable support tube is formed of a second material different from the first material.

18. The system of claim 10, wherein each tip of the plurality of selectable tips is configured to irrigate a sinus portion.

\* \* \* \* \*

UNITED STATES PATENT AND TRADEMARK OFFICE
CERTIFICATE OF CORRECTION

PATENT NO. : 11,266,776 B2
APPLICATION NO. : 14/928066
DATED : March 8, 2022
INVENTOR(S) : Jie Wen It is certified that error appears in the above-identified patent and that said Letters Patent is hereby corrected as shown below:

In the Specification

Column 2, Line 52, delete "allow" and insert --arrow-- therefor

Column 3, Line 41, delete "at at" and insert --at-- therefor

Column 3, Line 66, delete "82," and insert --82, 84-- therefor

In the Claims

Column 6, Line 37, in Claim 1, delete "ones" and insert --one-- therefor

Signed and Sealed this
Fourteenth Day of June, 2022

Katherine Kelly Vidal
*Director of the United States Patent and Trademark Office*